United States Patent
Saito et al.

(10) Patent No.: US 11,414,371 B2
(45) Date of Patent: Aug. 16, 2022

(54) METHOD FOR PRODUCING METHYL METHACRYLATE

(71) Applicant: ASAHI KASEI KABUSHIKI KAISHA, Tokyo (JP)

(72) Inventors: Hideyuki Saito, Tokyo (JP); Takamasa Ito, Tokyo (JP); Masahiko Idemoto, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 17/043,975

(22) PCT Filed: Apr. 15, 2020

(86) PCT No.: PCT/JP2020/016541
§ 371 (c)(1),
(2) Date: Sep. 30, 2020

(87) PCT Pub. No.: WO2020/261720
PCT Pub. Date: Dec. 30, 2020

(65) Prior Publication Data
US 2021/0047261 A1 Feb. 18, 2021

(30) Foreign Application Priority Data
Jun. 28, 2019 (JP) .............................. JP2019-121444

(51) Int. Cl.
| | | |
|---|---|---|
| *C07C 67/58* | (2006.01) | |
| *B01D 3/14* | (2006.01) | |
| *B01D 3/00* | (2006.01) | |
| *B01D 3/34* | (2006.01) | |
| *C08F 20/18* | (2006.01) | |

(52) U.S. Cl.
CPC .............. *C07C 67/58* (2013.01); *B01D 3/007* (2013.01); *B01D 3/143* (2013.01); *B01D 3/34* (2013.01); *C08F 20/18* (2013.01)

(58) Field of Classification Search
CPC ......... C07C 69/54; C07C 67/42; C07C 67/54; C07C 67/58; C08F 212/24; C08F 220/382; C08F 212/32; C08F 20/18; C08F 220/1806; C08F 220/1811; C08F 220/365; C08F 220/585; C08F 220/1808; B01D 3/007; B01D 3/143; B01D 3/34; B01D 3/40; C09D 125/18; G03F 7/0045; G03F 7/039; G03F 7/0392; G03F 7/0397
See application file for complete search history.

(56) References Cited

U.S. PATENT DOCUMENTS

| | | | |
|---|---|---|---|
| 5,969,178 A | 10/1999 | Okamoto et al. | |
| 6,680,405 B1 | 1/2004 | Munetou et al. | |
| 2008/0009405 A1* | 1/2008 | Russell | F22B 1/1838 502/56 |
| 2016/0200660 A1* | 7/2016 | Krill | C07C 45/75 560/208 |
| 2017/0247312 A1 | 8/2017 | Kuvadia et al. | |
| 2021/0113997 A1* | 4/2021 | Limbach | B01J 35/002 |

FOREIGN PATENT DOCUMENTS

| | | | |
|---|---|---|---|
| JP | 58 157740 | * | 9/1983 |
| JP | 58-157740 A | | 9/1983 |
| JP | 11-246453 A | | 9/1999 |
| JP | 2006-225401 A | | 8/2006 |
| JP | 3819419 B2 | | 9/2006 |
| JP | 2017-533208 A | | 11/2017 |
| WO | WO 2015/055843 A1 | | 4/2015 |

OTHER PUBLICATIONS

JP 58 157740 translated (Year: 1983).*
Supplementary European Search Report for European Application No. 20761491.8, dated Mar. 12, 2021.
International Preliminary Report on Patentability and English translation of the Written Opinion of the International Searching Authority for International Application No. PCT/JP2020/016541, dated Jan. 6, 2022.
English translation of International Search Report for International Application No. PCT/JP2020/016541, dated Jun. 23, 2020.

* cited by examiner

*Primary Examiner* — Brandon J Fetterolf
*Assistant Examiner* — Blaine G Doletski
(74) *Attorney, Agent, or Firm* — Birch, Stewart, Kolasch & Birch, LLP (57) ABSTRACT

A method for producing methyl methacrylate including:
a distillation step including:
supplying a reaction solution, which is obtained by subjecting methacrolein, methanol, and molecular oxygen to oxidative esterification in an oxidative esterification reactor and which contains the methyl methacrylate as a reaction product, to a first distillation column located at downstream of the oxidative esterification reactor,
extracting a fraction containing the methacrolein and the methanol from a medium section of the first distillation column, and
extracting a column bottom liquid containing the methyl methacrylate from a column bottom of the first distillation column,
wherein a concentration of the methanol in the column bottom liquid is 1% by mass or more and 30% by mass or less.

16 Claims, 4 Drawing Sheets

METHOD FOR PRODUCING METHYL METHACRYLATE

TECHNICAL FIELD

The present invention relates to a method for producing methyl methacrylate.

BACKGROUND ART

In recent years, intensive studies have been made on a method in which methacrolein, methanol, and molecular oxygen are subjected to an oxidative esterification reaction to produce methyl methacrylate at a time (hereinafter, merely referred to as "direct ML-to-MMA method"). In the direct ML-to-MMA method, a reaction is performed using an excess of methanol relative to methacrolein, so that a reaction solution is obtained as a mixed solution containing unreacted methacrolein, unreacted methanol, methyl methacrylate which is a reaction product, and water and methacrylic acid which are reaction by-products. The reaction is performed in the presence of the excess of methanol in the direct ML-to-MMA method, so that the unreacted methanol is desirably collected and recycled from an economic perspective.

Examples using the direct ML-to-MMA method include a method described in Patent Literature 1. In Patent Literature 1, the following method is proposed. A reaction solution obtained by the direct ML-to-MMA method, i.e., a mixed solution of methacrolein, methyl methacrylate, water, methacrylic acid, and methanol is supplied to a medium section of a distillation column, and the methacrolein and the methanol are azeotropic with each other in a concentration part of the distillation column. Then, residual methanol is azeotropic with a part of methyl methacrylate which is a reaction product, and extracted. The methanol and the methacrolein are simultaneously collected as a mixed solution with the methyl methacrylate. Here, according to the method described in Patent Literature 1, the methacrolein and the methanol are not substantially contained in a column bottom liquid of the distillation column. The method makes it possible to simultaneously collect the methacrolein and the methanol in a simple and short process using only one distillation column, and allows a long-term continuous operation.

CITATION LIST

Patent Literature

Patent Literature 1: Japanese Patent Publication No. 3819419

SUMMARY OF INVENTION

Technical Problem

When the methacrolein and the methanol are not substantially contained in the column bottom liquid of the distillation column based on the method described in Patent Literature 1, the concentration of the water in the column bottom liquid is high, so that the latent heat of vaporization of the column bottom liquid approaches that of the water. The latent heat of vaporization of the water is two or more times of that of the methanol, so that a quantity of heat required for operating the distillation column is increased compared with the case where the methanol is contained in the column bottom liquid. As a result, the consumption energy of a heat source is increased. When the methanol is not present in the column bottom liquid, a temperature in the distillation column also tends to be higher than that when the methanol is present, so that the occurrence of a polymer may lead to the blockage of the distillation column. Thus, from the viewpoint of reducing energy required for distillation, and suppressing the blockage of the distillation column to achieve a long-term stable operation, there is still room for improvement in the technique of Patent Literature 1.

The present invention has been made in view of the problems of the conventional technique, and an object of the present invention is to provide a method for producing methyl methacrylate which can achieve a more efficient and stable operation when the methyl methacrylate is produced.

Solution to Problem

As a result of conducting diligent research in view of those circumstances, the present inventors have found that the above problems can be solved by setting the concentration of methanol in a predetermined column bottom liquid to be within a specific range, and have completed the present invention.

That is, the present invention includes the following aspects.

[1] A method for producing methyl methacrylate, comprising:
a distillation step comprising
supplying a reaction solution, which is obtained by subjecting methacrolein, methanol, and molecular oxygen to oxidative esterification in an oxidative esterification reactor and which comprises the methyl methacrylate as a reaction product, to a first distillation column located at downstream of the oxidative esterification reactor,
extracting a fraction comprising the methacrolein and the methanol from a medium section of the first distillation column, and
extracting a column bottom liquid comprising the methyl methacrylate from a column bottom of the first distillation column,
wherein a concentration of the methanol in the column bottom liquid is 1% by mass or more and 30% by mass or less.

[2] The method for producing methyl methacrylate according to [1], further comprising a step of phase-separating the column bottom liquid into a light phase and a heavy phase.

[3] The method for producing methyl methacrylate according to [2], further comprising a step of distilling the heavy phase in a second distillation column to obtain a fraction comprising the methanol.

[4] The method for producing methyl methacrylate according to [3], wherein the fraction comprising the methanol obtained from the second distillation column is recycled to the oxidative esterification reaction.

[5] The method for producing methyl methacrylate according to any one of [2] to [4], further comprising a step of subjecting the light phase to purification, and a step of adding a polymerization inhibitor to the light phase after the purification.

[6] The method for producing methyl methacrylate according to any one of [1] to [5], further comprising a step of subjecting the methacrolein, the methanol, and the molecular oxygen to oxidative esterification in the oxidative esterification reactor, to obtain the reaction solution.

[7] The method for producing methyl methacrylate according to any one of [1] to [6], wherein the fraction, which comprises the methacrolein and the methanol and which has been extracted from the medium section of the first distillation column, is recycled to the oxidative esterification reaction.

[8] The method for producing methyl methacrylate according to any one of [1] to [7], wherein a methanol is further added to the first distillation column in the distillation step to adjust the concentration of the methanol in the column bottom liquid.

[9] The method for producing methyl methacrylate according to [8], wherein a ratio of the number of moles of the methanol to be further added, to the number of moles of the methacrolein contained in the reaction solution is 0.1 or more and 3.0 or less.

[10] The method for producing methyl methacrylate according to any one of [1] to [9], wherein, in the distillation step, a temperature of the column bottom of the first distillation column is 45° C. or higher and 80° C. or lower, and a pressure of the column bottom of the first distillation column is −50 kPaG or more and 0 kPaG or less.

[11] The method for producing methyl methacrylate according to any one of [1] to [10], wherein a residence time of the column bottom liquid of the first distillation column calculated by the following formula is 1.5 hours or less:

residence time (hour)=amount (kg) of column bottom liquid present in first distillation column/extraction amount (kg/hour) of column bottom liquid per unit time.

[12] The method for producing methyl methacrylate according to any one of [1] to [11], wherein a content rate of a medium boiling point material in the column bottom liquid in the first distillation column is 0.1% by mass or more.

[13] The method for producing methyl methacrylate according to [12], wherein the medium boiling point material comprises methyl acrylate.

[14] The method for producing methyl methacrylate according to any one of [1] to [13], wherein at least a part of the column bottom liquid is extracted, then heated by a heat-exchange with a vent gas generated from the oxidative esterification reactor, and thereafter returned to the column bottom of the first distillation column.

[15] The method for producing methyl methacrylate according to any one of [1] to [14],
wherein:
an amount of the methacrolein extracted from the medium section of the first distillation column is 95% by mass or more of an amount of the methacrolein contained in the reaction solution; and
an amount of the methanol extracted from the medium section of the first distillation column is 70% by mass or more of an amount of the methanol contained in the reaction solution.

[16] The method for producing methyl methacrylate according to any one of [1] to [15], further comprising a step of cooling a column top gas out of the first distillation column to obtain a condensate, wherein a concentration of the methanol in the condensate is 30% by mass or less.

Advantageous Effects of Invention

The present invention can achieve a more efficient and stable operation when methyl methacrylate is produced.

DESCRIPTION OF EMBODIMENTS

Hereinafter, an embodiment of the present invention (hereinafter, also referred to as "the present embodiment") will be described in detail. The present invention is not limited to the following present embodiment, and may be carried out as variously modified within the scope of the present invention.

A method for producing methyl methacrylate according to the present embodiment comprises:
a distillation step comprising
supplying a reaction solution, which is obtained by subjecting methacrolein, methanol, and molecular oxygen to oxidative esterification in an oxidative esterification reactor and which comprises the methyl methacrylate as a reaction product, to a first distillation column located at downstream of the oxidative esterification reactor,
extracting a fraction comprising the methacrolein and the methanol from a medium section of the first distillation column, and
extracting a column bottom liquid comprising the methyl methacrylate from a column bottom of the first distillation column,
wherein a concentration of the methanol in the column bottom liquid is 1% by mass or more and 30% by mass or less. With this constitution, the method for producing methyl methacrylate according to the present embodiment can achieve a more efficient and stable operation when the methyl methacrylate is produced.

Figure 1:
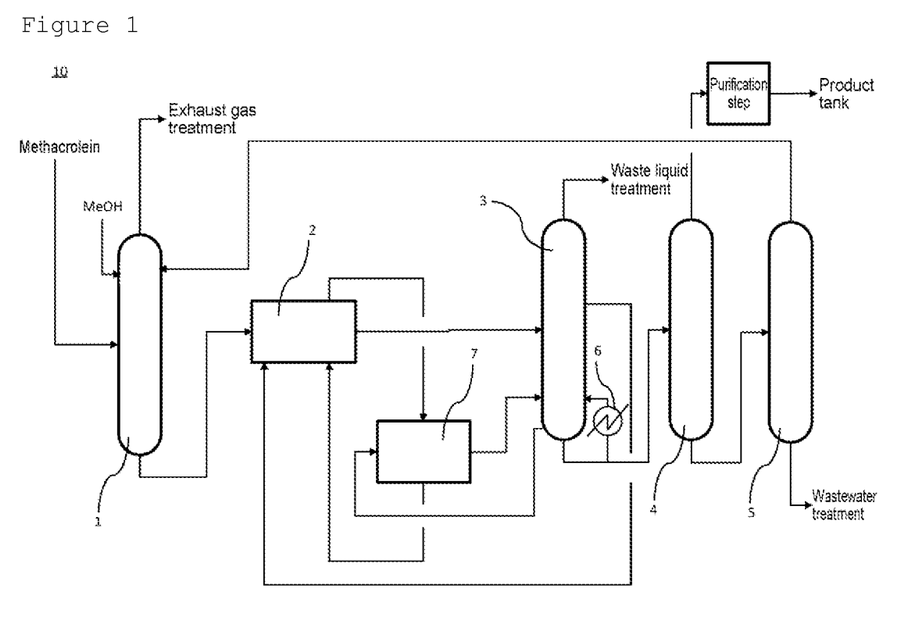
FIG. 1 illustrates a schematic diagram exemplifying an example of a producing device which can be applied to a method for producing methyl methacrylate according to the present embodiment.

First, an example of a producing device which can be applied to the method for producing methyl methacrylate according to the present embodiment will be described using FIG. 1. As shown in FIG. 1, a producing device 10 includes a methacrolein absorber column 1, an oxidative esterification reactor 2, a first distillation column 3, a phase separator 4, a second distillation column 5, a first heat exchanger unit 6, and a second heat exchanger unit 7.

In the methacrolein absorber column 1, a methacrolein-containing gas and methanol are subjected to gas-liquid contact to cause the methanol to absorb methacrolein. In the oxidative esterification reactor 2 located between the methacrolein absorber column 1 and the first distillation column 3, the methacrolein and the methanol (in the drawing, described as "MeOH") are subjected to oxidative esterification in the presence of a catalyst while molecular oxygen is supplied, whereby a reaction solution can be obtained. In the oxidative esterification reactor 2, conditions of an oxidative esterification reaction step to be described later can be applied. The reaction solution is supplied to the first distillation column 3 located at downstream of the oxidative esterification reactor 2. In the oxidative esterification reactor, the first distillation column is located at downstream of the last reactor. That is, an example in which oxidative esterification is carried out in one oxidative esterification reactor 2 is shown in FIG. 1, but a plurality of oxidative esterification reactors may be serially installed. In this case, the first distillation column is disposed further downstream of an oxidative esterification reactor located at the lowermost stream.

Then, the reaction solution supplied to the first distillation column 3 is subjected to distillation. A column bottom liquid which is present at the column bottom of the first distillation column 3 is heated, to perform distillation in the first distillation column 3. The column bottom liquid may be extracted from the column bottom of the first distillation column 3, and supplied to the phase separator 4. In this context, a part of the column bottom liquid may be supplied to the first heat exchanger unit 6, then heated, and thereafter returned to the column bottom of the first distillation column 3. Thereby, heating for distillation can be performed. As the first heat exchanger unit 6, a reboiler is used, for example. Heat is externally supplied to the first heat exchanger unit 6 from a heat medium such as a vapor or a liquid, to heat the column bottom liquid. The second heat exchanger unit 7 may be provided to collect the heat from the oxidative esterification reactor 2, thereby heating the column bottom liquid by heat exchange. For example, at least a part of the column bottom liquid which is present at the column bottom of the first distillation column 3 may be extracted, then heated in the second heat exchanger unit 7, and thereafter returned to the column bottom of the first distillation column 3 for heating. The methacrolein and the methanol collected from the first distillation column 3 can be recycled to an oxidative esterification reaction. Specifically, the methacrolein and the methanol can be recycled to the methacrolein absorber column 1 and/or the oxidative esterification reactor 2.

The column bottom liquid of the first distillation column 3 is supplied to the phase separator 4 located at downstream of the first distillation column 3. In the phase separator 4, the column bottom liquid is phase-separated into a light phase and a heavy phase. The light phase separated in the phase separator 4 is collected as methyl methacrylate as a product through a purification step.

Figure 4:
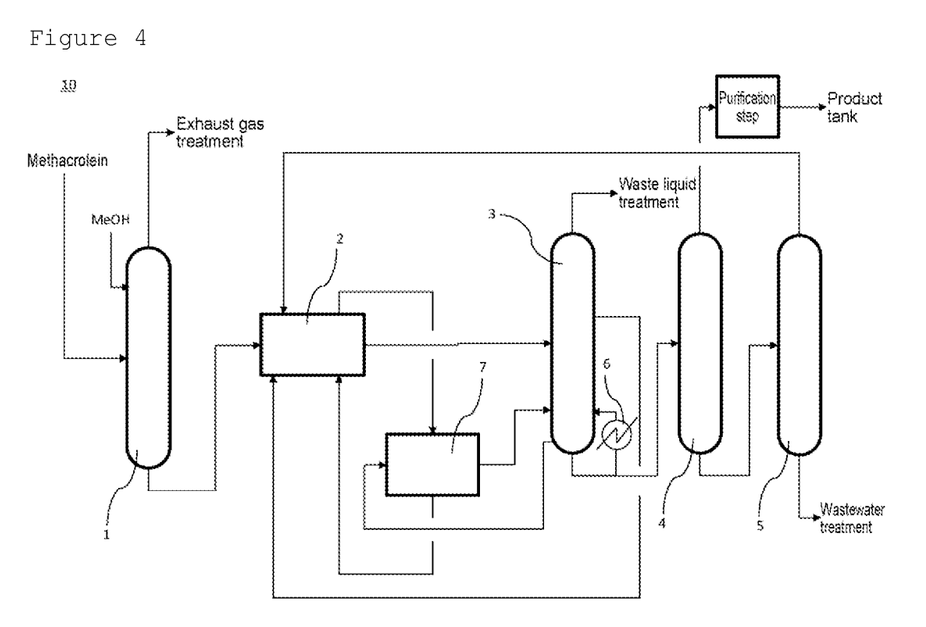
FIG. 4 illustrates a schematic diagram showing an example when a fraction containing methanol obtained from a second distillation column is recycled to an oxidative esterification reactor.

The heavy phase separated from the phase separator 4 can be distilled in the second distillation column 5 to obtain a fraction $F_2$ containing the methanol. The collected methanol can be recycled to the oxidative esterification reaction. Specifically, as shown in FIG. 1, the methanol can be recycled to the methacrolein absorber column 1. The collected methanol may be recycled to the oxidative esterification reactor 2, as shown in FIG. 4. Furthermore, the collected methanol may be recycled to both the methacrolein absorber column 1 and the oxidative esterification reactor 2.

Hereinafter, each of steps will be described in detail.
(Oxidative Esterification Reaction Step)

The method for producing methyl methacrylate according to the present embodiment may include a step (merely referred to as "oxidative esterification reaction step") of subjecting methacrolein, methanol, and molecular oxygen to oxidative esterification in an oxidative esterification reactor, to obtain a reaction solution. In the oxidative esterification reaction step, alkalis such as a sodium hydroxide aqueous solution may be added in order to adjust pH in the reactor to about 6 to 7, and therefore, alkali salts derived from the alkalis may be contained in the reaction solution obtained through the oxidative esterification step.

The reaction solution can be obtained as a mixture containing methyl methacrylate in the oxidative esterification reaction step (direct ML-to-MMA method). Typically, the reaction solution may contain unreacted methacrolein, unreacted methanol, methyl methacrylate which is a reaction product, water, methacrylic acid or its alkali salt, acetone, and methyl acrylate. The oxidative esterification reaction step is not particularly limited, and can be carried out by employing known reaction conditions using known reaction raw materials and reaction facilities.

A catalyst fed to the oxidative esterification reactor at this time is not particularly limited, and for example, a heterogeneous catalyst is preferably used, in which nickel having an oxidation state and gold are supported on a carrier such as silica, for example.
(Distillation Step)

In the distillation step, first, a reaction solution obtained by subjecting methacrolein, methanol, and molecular oxygen to oxidative esterification in an oxidative esterification reactor, and containing methyl methacrylate as a reaction product is supplied to a first distillation column. The reaction solution may be the reaction solution obtained in the above-mentioned oxidative esterification reaction step.

As described above, in the method for producing methyl methacrylate according to the present embodiment, at least the first distillation column is used. The constitution of the first distillation column is not particularly limited as long as the reaction solution can be externally supplied to the first distillation column; the column bottom liquid containing the methyl methacrylate from the column bottom can be collected; and components separated from the medium section can be extracted, and one having a known constitution can be employed. That is, the form of the first distillation column is not particularly limited, and the first distillation column may be a tray column or a packed column. The tray column may include a sieve tray, a cascade tray, a turbo grid tray, a ripple tray, and a dual tray and the like without limitation. In the case of the packed column, a regular filling material such as Mellapack and an irregular filling material such as a cascade mini-ring can be employed without limitation. In the present embodiment, the methacrolein and the methyl methacrylate which are easily polymerizable materials are subjected to distillation separation, so that the form of a column having a structure which is less likely to be blocked with a high-boiling substance or a polymer, or a structure which easily removes a blocking matter is preferable. In particular, blockage caused by the formation and concentration of the high-boiling substance or polymer is apt to occur in the vicinity of the column bottom serving as a collecting part of the column bottom liquid containing the methyl methacrylate, whereby the tray column is preferably used as the distillation column. The form of distillation in the first distillation column may be a batch type or a continuous type, and is preferably a continuous type.

The reaction solution supplied to the first distillation column is distilled, and a part thereof is accumulated at the bottom in the column. In the present embodiment, a portion in which the solution is accumulated at the bottom of the first distillation column is particularly referred to as column bottom; a liquid which is present at the column bottom is particularly referred to as column bottom liquid; and a portion other than the column bottom and the column top is referred to as medium section. The composition of a fraction extracted from the medium section is usually different from that of the column bottom liquid or column top gas.

In the present embodiment, as long as the reaction solution is supplied to the first distillation column, a supply position is not particularly limited. From the viewpoint of achieving a more efficient and stable operation, the supply position is preferably the medium section.

Then, in the distillation step, the reaction solution is supplied to the first distillation column located at downstream of the oxidative esterification reactor, to distill the reaction solution. A fraction $F_1$ containing the methacrolein and the methanol is extracted from the medium section of the first distillation column, and the column bottom liquid containing the methyl methacrylate is extracted from the column bottom of the first distillation column. At this time, the concentration of the methanol in the column bottom liquid is set to 1% by mass or more and 30% by mass or less. A specific example of the operation is as follows. That is, at least a part of methacrolein and methanol are separated and collected from the reaction solution which contains methacrolein, methyl methacrylate, water, sodium methacrylate, and methanol and is supplied to the first distillation column. At this time, the methacrolein and the methanol are azeotropic with each other, extracted from the medium section of the first distillation column, and the first distillation column is operated so that the concentration of the methanol in the mixed solution which contains the methyl methacrylate, the water, and the methanol and is obtained from the column bottom of the first distillation column is set to 1% by mass or more and 30% by mass or less, to collect the methacrolein from the first distillation column. More specifically, the concentration of the methanol of the column bottom liquid can be adjusted by controlling a supply amount of heat (for example, a supply amount of steam to a reboiler) to a heat exchanger unit, and an extraction amount from the medium section of the first distillation column using the temperature of the column bottom of the first distillation column as an index. For example, when the pressure of the column bottom is set to −3 kPaG, and the amount of steam and the extraction amount from the medium section are operated so that the temperature of the column bottom is set to about 85° C., the concentration of the methanol tends to be less than 1% by mass. When the supply amount of heat to the heat exchanger unit and the extraction amount from the upper part are operated so that the temperature of the column bottom is set to about 78° C. at the same pressure, the concentration of the methanol tends to be 1% by mass or more and 30% by mass or less. Furthermore, when the supply amount of heat to the heat exchanger unit and the extraction amount from the medium section are operated so that the temperature of the column bottom is set to about 68° C. at the same pressure, the concentration of the methanol tends to be more than 30% by mass. However, the above typical examples are merely shown, and preferably appropriately adjusted based on various conditions such as the composition and the like of the reaction solution before being supplied to the first distillation column.

In the present embodiment, the concentration of the methanol in the column bottom liquid is set to 1% by mass or more and 30% by mass or less, whereby the methyl methacrylate can be more efficiently and stably produced.

When the concentration of the methanol in the column bottom liquid is less than 1% by mass, i.e., when the column bottom liquid does not substantially contain the methanol, the concentration of the water in the column bottom liquid is high, so that the latent heat of vaporization of the column bottom liquid approaches that of the water. The latent heat of vaporization of the water is two or more times of that of the methanol, so that a quantity of heat required for operating the distillation column is increased compared with the case where the methanol is contained in the column bottom liquid. As a result, for example, the steam flow rate or the like of the reboiler as the heat source is increased. Furthermore, when the methanol is not present in the column bottom liquid, an in-column temperature tends to be higher than that when the methanol is present, which may lead to the occurrence of a polymer. Furthermore, as described later, also during heat exchange with a vent gas from the oxidative esterification reactor, the temperature of the column bottom liquid itself also tends to be high, which makes it difficult to secure a sufficient temperature difference when the column bottom liquid is heat-exchanged with a fluid having a higher temperature than that of the column bottom liquid in a producing process, so that the efficiency of heat recovery can be hardly said to be sufficient.

Meanwhile, when the concentration of the methanol in the column bottom liquid is 1% by mass or more, the concentration of the water in the column bottom liquid is decreased, which causes decreased latent heat of vaporization, whereby energy required for evaporation is decreased. Therefore, the amount of steam required for the operation can be reduced, which accordingly contributes to reduction of running cost. Furthermore, the temperature of the column bottom liquid tends to be decreased, so that the in-column temperature of the first distillation column also tends to be decreased.

The polymer is generally apt to occur at a higher temperature, whereby the in-column temperature is decreased to suppress the occurrence of the polymer in the column, which makes it possible to operate the distillation column over a longer period of time. In particular, the temperature of the column bottom which is the highest temperature in the column is decreased. Accordingly, the saturation temperature of the steam supplied to the reboiler can be decreased, which leads to the prevention of the blockage caused by the occurrence of the polymer in the reboiler.

From the viewpoint described above, the concentration of the methanol in the column bottom liquid is preferably 8% by mass or more, and more preferably 15% by mass or more.

Meanwhile, when the concentration of the methanol in the column bottom liquid is more than 30% by mass, the column bottom liquid forms a homogeneous phase, and is not separated into two phases. That is, the column bottom liquid is hardly separated into the light layer containing the methyl methacrylate and the like and the heavy phase containing the water and the methanol. In order to prevent such an inconvenience, the concentration of the methanol in the column bottom liquid is set to 30% by mass or less.

The concentration of the methanol in the column bottom liquid is preferably 27% by mass or less, and more preferably 20% by mass or less. The concentration of the methanol is within such a range, whereby a time required for separating the light phase and the heavy phase from each other can be reduced, and the precipitation of alkali salts tends to be suppressed in subsequent distillation to allow the fraction containing the methanol to be efficiently recovered. As described later, when the heavy phase is distilled in the second distillation column, the concentration of the methanol in the column bottom liquid is within the above-mentioned range, which tends to allow the precipitation of the salts in the distillation column to be suppressed.

As described above, when heat recovery is carried out from the oxidative esterification reactor, the method for producing methyl methacrylate according to the present embodiment secures a large temperature difference with a recovery heat source (for example, high-temperature fluid) from the oxidative esterification reactor when the temperature of the column bottom is lower, whereby the amount of heat recovery is increased, which makes it possible to reduce the quantity of heat supplied from the heat source. As a result, this contributes to reduction of running cost. In particular, the temperature of the vent gas generated from the oxidative esterification reactor is equal to the internal temperature of the oxidative esterification reactor. The internal temperature is preferably, for example, 60 to 120° C. When the vent gas is processed as an exhaust gas as it is in such a temperature range, excessive heat losses occur. Meanwhile, waste heat from the reactor can be collected by setting the temperature of the column bottom liquid of the first distillation column to be equal to or lower than the temperature of the vent gas for heat exchange. Furthermore, the difference in temperature between the column bottom liquid and the vent gas is increased as much as possible, which leads to increase in the amount of heat recovery. In addition, as a result of heat exchange, the vent gas is cooled, and a valuable substance such as methacrolein or methanol contained in the vent gas condenses. This can also be collected as a reaction raw material. From the above viewpoint, in the present embodiment, it is preferable that at least a part of the column bottom liquid is heated by heat exchange with the vent gas generated in the oxidative esterification reactor, and the column bottom liquid after the heat exchange is resupplied to the first distillation column.

In the distillation step in the present embodiment, the fraction $F_1$ containing the methacrolein and the methanol is collected from the medium section of the first distillation column. The recovery position is not particularly limited as long as it is the medium section of the first distillation column, and the recovery position is preferably above the supply portion of the reaction solution. The methacrolein collected from the medium section of the first distillation column is preferably 95% by mass or more of the methacrolein contained in the reaction solution supplied to the first distillation column. Furthermore, the methanol collected from the medium section of the first distillation column is preferably 70% by mass or more of the methanol contained in the reaction solution supplied to the first distillation column.

The method for producing methyl methacrylate according to the present embodiment preferably recycles the fraction $F_1$ containing the methacrolein and the methanol and extracted from the medium section of the first distillation column to the oxidative esterification reaction. Specifically, the method preferably recycles the fraction $F_1$ containing the methacrolein and the methanol to the methacrolein absorber column and/or the oxidative esterification reactor.

In the method described in Patent Literature 1, the methyl methacrylate and the methyl acrylate which is an impurity, and the like are azeotropic with the methanol. Therefore, when the methyl methacrylate and the methyl acrylate and the like are recycled to the reaction step together with the methacrolein and methanol to be collected, the content rates of the methyl methacrylate and methyl acrylate and the like in the reaction solution are increased over time, and the content rates of the methacrolein and methanol are decreased to cause an increased amount of occurrence of a by-product other than the methyl methacrylate, which causes a decreased reaction yield of the methyl methacrylate. In particular, almost the total amount of a medium boiling point material such as methyl acrylate is recycled to the reaction step together with the methacrolein and the methanol, which make it necessary to extract the medium boiling point material to steps other than the reaction step together with the collected methacrolein and methanol, and discard the medium boiling point material in order to prevent the recycle. This causes decreased recovery rates of the methacrolein and methanol. As a result, the methacrolein and the methanol which are raw materials, and the methyl methacrylate which is a product are lost in large amounts. As described above, the reaction solution is distilled in a state where the concentration of the methanol in the column bottom liquid is set to be within a specific range, and the fraction $F_1$ containing the methacrolein and the methanol and extracted from the medium section is recycled to the oxidative esterification reaction, whereby the decrease in the reaction yield in the oxidative esterification reactor is suppressed.

The methyl methacrylate in the fraction $F_1$ from the medium section is not particularly limited, and from the above viewpoint, the amount of the methyl methacrylate is preferably 20.0% by mass or less, more preferably 15.0% by mass or less, and still more preferably 12.0% by mass or less.

In addition to the above, in the distillation step, a methanol may further be added to the first distillation column, whereby the concentration of the methanol in the column bottom liquid can also be adjusted. The phrase "a methanol may further be added to the first distillation column" means that such methanol is added to the distillation column from a route different from that of the reaction solution. In such embodiment, the concentration of the methanol tends to be more easily adjusted, which is preferable.

Figure 2:
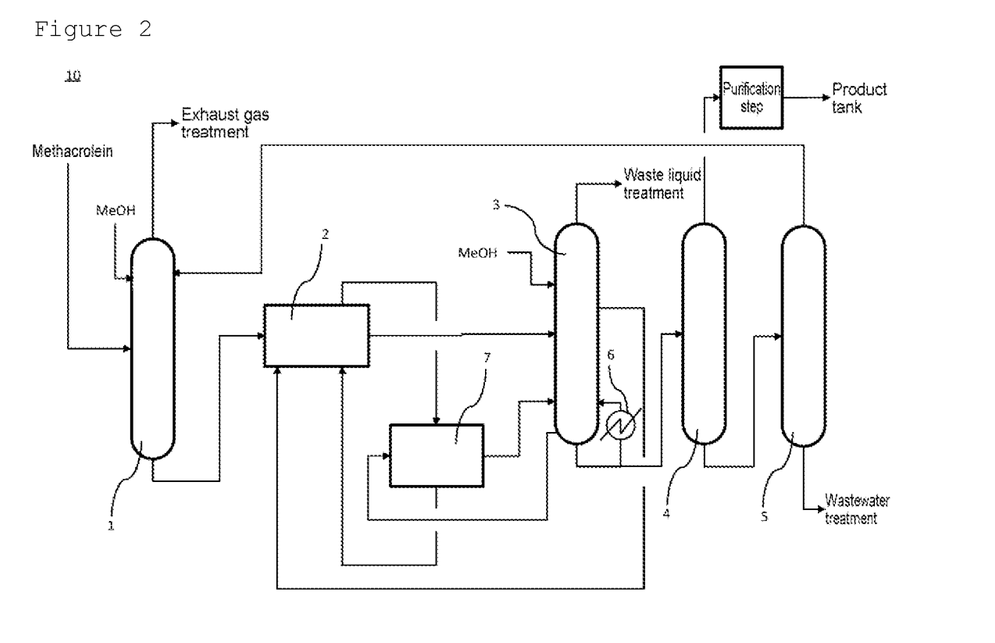
FIG. 2 illustrates a schematic diagram showing an example when methanol is added to a first distillation column from a route different from that of a reaction solution.

As the different route, for example, a methanol supply part is provided at a different position from a supply portion of the reaction solution in the first distillation column, and the methanol is added to the methanol supply part, whereby the concentration of the methanol in the column bottom liquid can be increased (for example, see FIG. 2). The position of the methanol supply part is not particularly limited, and the methanol supply part is preferably located within the medium section.

Figure 3:
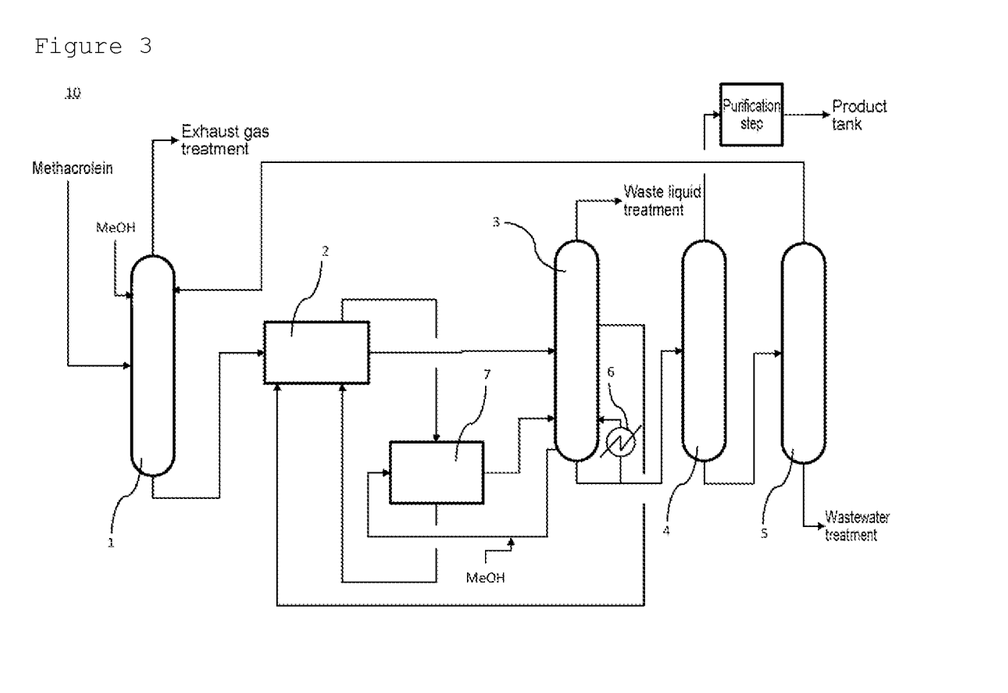
FIG. 3 illustrates a schematic diagram showing another example when methanol is added to a first distillation column from a route different from that of a reaction solution.

Methanol is added to a circulation system related to a heat recovery step as exemplified in FIG. 1 as the different route, whereby an embodiment in which the methanol is indirectly added to the first distillation column can also be employed (for example, see FIG. 3). In this case, the temperature of the column bottom liquid which circulates at the temperature of the methanol to be add can also be lowered, which makes it possible to secure a large temperature difference during heat exchange, whereby the operation is preferably performed from the viewpoint of further improving a heat recovery efficiency.

In the present embodiment, from the viewpoint of more easily adjusting the concentration of the methanol, the ratio of the number of moles of the methanol added from the different route to the number of moles of the methacrolein contained in the reaction solution is preferably 0.1 or more and 3.0 or less.

From the same viewpoint described above, the ratio is more preferably 0.5 or more and 2.5 or less, and still more preferably 1.0 or more and 2.0 or less.

In the present embodiment, from the viewpoint of adjusting the concentration of the methanol in the column bottom liquid to the above-mentioned range, and lowering the in-column temperature to prevent the occurrence of the polymer, thereby easily performing a longer-term operation, it is preferable that, in the distillation step, the temperature of the column bottom of the first distillation column is 45°

C. or higher and 80° C. or lower, and the pressure of the column bottom of the first distillation column is −50 kPaG or more and 0 kPaG or less.

From the same viewpoint described above, it is preferable that the temperature of the column bottom of the first distillation column is more preferably 50° C. or higher and 77° C. or lower, and still more preferably 55° C. or higher and 73° C. or lower at the same pressure.

In the present embodiment, from the viewpoint of setting a residence time in the column bottom to a prescribed time or less to prevent the occurrence of the polymer, thereby easily performing a longer-term operation, the residence time of the column bottom liquid of the first distillation column calculated according to the following formula is preferably 1.5 hours or less.

residence time (hour)=amount (kg) of column bottom liquid present in first distillation column/extraction amount (kg/hour) of column bottom liquid per unit time From the same viewpoint described above, the residence time is more preferably 1 minute or more and 1.0 hour or less, still more preferably 1 minute or more and 45 minutes or less, yet still more preferably 5 minutes or more and 30 minutes or less, and even yet still more preferably 5 minutes or more and 15 minutes or less.

Steps following the distillation step are not particularly limited, and the purity of the methyl methacrylate collected as the column bottom liquid can be increased depending on the applications of the methyl methacrylate as an end product, or predetermined components can be recycled in consideration of the reaction yield.

From the viewpoint of collecting higher purity methyl methacrylate and further improving the reaction yield, it is preferable that the present embodiment further includes a step of phase-separating the column bottom liquid collected in the distillation step into a light phase and a heavy phase. The light phase corresponds to an oil phase containing the methyl methacrylate, and the heavy phase corresponds to an aqueous phase containing the methanol. The phase separator is not particularly limited, and various known phase separators can be employed. Specific examples thereof include, but are not limited to, a decanter, an extraction column, and a centrifugal separator. These may be combined and disposed in series. Before the step of phase-separating the column bottom liquid into the light phase and the heavy phase, it is more preferable to add a strong acid, and optionally water, followed by mixing, decompose methacrolein dimethyl acetal and the like which may be contained in the reaction solution, and neutralize sodium methacrylate for phase-shifting as methacrylic acid to the light phase.

It is preferable that the present embodiment further includes a step of distilling the heavy phase in the second distillation column to obtain a fraction $F_2$ containing the methanol.

The constitution and form of the second distillation column are not particularly limited, and may be the same as those of the first distillation column.

In the present embodiment, the fraction $F_2$ containing the methanol and obtained from the second distillation column is preferably recycled to the oxidative esterification reaction. Specifically, the fraction $F_2$ containing the methanol is preferably recycled to the methacrolein absorber column and/or the oxidative esterification reactor. That is, as exemplified in FIG. 1, the fraction $F_2$ containing the methanol may be recycled to the methacrolein absorber column 1. As exemplified in FIG. 4, the fraction $F_2$ containing the methanol may be recycled to the oxidative esterification reactor 2.

In the present embodiment, a certain amount of the methanol as the column bottom liquid is extracted in the first distillation column, whereby the fraction $F_2$ containing the methanol obtained from the second distillation column is preferably recycled to the oxidative esterification reaction from the viewpoint of further improving an operation efficiency. The fraction $F_2$ preferably contains 50% by mass or more of the methanol.

In the present embodiment, when an operation condition during distillation is adjusted so that the concentration of the methanol in the column bottom liquid extracted from the first distillation column is set to 1% by mass or more, the content rate of the medium boiling point material in the column bottom liquid is significantly increased compared with the case where the concentration of the methanol is adjusted to less than 1% by mass. This is because, when an operation condition in which the methanol is present in the column bottom liquid extracted from the first distillation column is employed, the medium boiling point material remains in the column bottom liquid together with the methanol without being completely extracted from the medium section. Thus, the medium boiling point material is present in the column bottom liquid collected from the first distillation column, so that the content rate of the medium boiling point material of the extraction liquid from the medium section is relatively decreased.

The medium boiling point material is a substance having a boiling point between an azeotropic point (60.0° C.) of the methacrolein and methanol and a boiling point (64.5° C.) of the methyl methacrylate and methanol, or a substance which is azeotropic with a substance present in a reaction solution such as methanol, methacrolein, or water, so that an azeotropic point is set to be within the above range. For example, the methyl acrylate alone has a boiling point of 86.1° C. The methyl acrylate has an azeotropic property with the methanol and has an azeotropic point of 62.5° C., which corresponds to the medium boiling point material.

When the property is utilized, distillation is performed in order to separate the column bottom liquid collected from the column bottom of the first distillation column into the light phase and the heavy phase in subsequent steps, and separate a low boiling point material from the light phase, whereby the medium boiling point material such as methyl acrylate can be densely concentrated together with the low boiling point material, and extracted. Most low-boiling point impurities such as acetone besides methyl acrylate are present in the extraction liquid, whereby, even if the extraction liquid is discarded, substances such as methacrolein, methanol, and methyl methacrylate are hardly lost. Furthermore, the distillation column used at this time may be formed independently of the first distillation column, and it is not necessary to employ a distillation column having a novel constitution. For example, conventionally known distillation columns such as the distillation column for separating the low boiling point material used in Patent Literature 1 can be employed. This can easily eliminate a problem in that the medium boiling point component is densely concentrated in the oxidative esterification reaction step. The problem may be caused in Patent Literature 1.

The methyl methacrylate contained in the reaction solution is azeotropic with the methanol, compared with the method described in Patent Literature 1, so that the methyl methacrylate is less likely to be extracted from the medium section of the first distillation column. Therefore, the content rate of the methyl methacrylate in the fraction $F_1$ from the medium section of the first distillation column can also be reduced. The fraction $F_1$ is recycled to the oxidative esterification reactor, which accordingly contributes to increases in the concentrations of the methacrolein and methanol in the oxidative esterification reaction step, to provide an improved reaction yield. In this regard, in the method of Patent Literature 1, the medium boiling point material is not substantially present in the column bottom, and almost the total amount of the medium boiling point material is present in the fraction $F_1$ from the medium section. For this reason, it is necessary to subject a part of the fraction $F_1$ from the medium section to a discarding treatment in order to separate the medium boiling point material. The methacrolein, the methanol, and the methyl methacrylate make up the majority of the fraction $F_1$ from the medium section, so that the valuable substances are lost in large amounts in the discarding treatment.

However, in the present embodiment, a part of the fraction $F_1$ from the medium section may be subjected to the discarding treatment to further reduce the concentration of the medium boiling point component in the oxidative esterification reaction. In this case, the content rate of the medium boiling point material in the fraction $F_1$ from the medium section is lower than that of the method of Patent Literature 1, whereby it is preferable that the fraction $F_1$ from the medium section is distilled in one or more distillation columns, and the methacrolein, the methanol, and the methyl methacrylate are separated and collected, followed by discarding the medium boiling point material.

The content rate of the medium boiling point material in the column bottom liquid collected from the first distillation column is not particularly limited, and is preferably 0.1% by mass or more, more preferably 0.5% by mass or more, still more preferably 1.0% by mass or more, and yet still more preferably 2.0% by mass or more from the above viewpoint. In the present embodiment, when the medium boiling point material contains the methyl acrylate, the concentration of the methyl acrylate is preferably 0.1% by mass or more, more preferably 0.5% by mass or more, and still more preferably 1.0% by mass or more.

The content rate of the medium boiling point material in the fraction $F_1$ from the medium section is not particularly limited, and is preferably 10.0% by mass or less, more preferably 7.0% by mass or less, still more preferably 4.0% by mass or less, yet still more preferably 3.0% by mass or less, and even yet still more preferably 1.0% by mass or less from the above viewpoint. In the present embodiment, when the medium boiling point material contains the methyl acrylate, the content rate of the methyl acrylate in the fraction $F_1$ from the medium section is preferably 10.0% by mass or less, more preferably 7.0% by mass or less, still more preferably 4.0% by mass or less, yet still more preferably 3.0% by mass or less, and even yet still more preferably 1.0% by mass or less.

In the present embodiment, the gas extracted from the column top of the first distillation column can be cooled with a condenser to provide a condensate. It is preferable that a part of the condensate is supplied as a reflux liquid to a column top part of the first distillation column, and the remaining condensate is extracted out of the system and subjected to a discarding treatment and the like in order to prevent the concentration of a light boiling point material such as acetone. Therefore, the concentration of the methanol in the condensate is preferably as low as possible. Specifically, the concentration of the methanol in the condensate is preferably 30% by mass or less.

In the present embodiment, reaction by-products other than methyl methacrylate and methacrylic acid are contained as impurities in the light phase obtained by phase-separating the column bottom liquid of the first distillation column. Some of the impurities may have an influence on qualities such as hue of a product, whereby the impurities are desirably purified and removed. The purification method is not particularly limited, and is generally a method utilizing a boiling point difference with methyl methacrylate. For example, a fraction containing methyl methacrylate can be obtained by distillation in the distillation column.

The purified light phase is apt to cause the polymerization of the methyl methacrylate, whereby a polymerization inhibitor is preferably added. The kind of the polymerization inhibitor to be added is not particularly limited, and 2,4-dimethyl-6-tert-butylphenol or the like is preferable.

EXAMPLES

Hereinafter, the present embodiment will be more specifically described giving Examples, but the present embodiment is in no way limited to Examples described below. Evaluation methods of physical properties are as described below.

Example 1

Methyl methacrylate was produced as follows using a producing device having the same constitution as that of a producing device exemplified in FIG. 1. The producing device was operated for one year according to the following set of procedures. Values such as amounts of components in Examples are values after reaching a steady operation. In a methacrolein absorber column, a methacrolein-containing gas and methanol were subjected to gas-liquid contact to cause the methanol to absorb methacrolein, and a mixed solution of the methacrolein and the methanol was sent to an oxidative esterification reactor. In the oxidative esterification reactor, an oxygen-containing gas was supplied to the mixed solution of the methacrolein and the methanol in the presence of a catalyst, to subject the mixed solution to an oxidative esterification reaction. At this time, a sodium hydroxide aqueous solution was added into the reactor so that pH in the reactor was set to 7.0. The composition of the reaction solution obtained by the reaction contained 8.1% by mass of methacrolein, 37.0% by mass of methyl methacrylate, 8.0% by mass of water, 1.5% by mass of sodium methacrylate, 40.0% by mass of methanol, 3.0% by mass of acetone, and 2.4% by mass of methyl acrylate. The reaction solution containing methacrolein, methyl methacrylate, water, sodium methacrylate, methanol, acetone, and methyl acrylate was supplied to a first distillation column. Here, as the first distillation column, a tray distillation column having a diameter of 10 cm and a height of 6 m and provided with 45-stage sieve trays was used. The reaction solution was supplied in an amount of 633.6 g/h from a 30th stage position as counted from a column top of the distillation column. Hydroquinone as a polymerization inhibitor was supplied from the column top so that the concentration of the polymerization inhibitor in the liquid falling inside the column was set to 100 mass ppm or more.

Distillation was carried out as follows. That is, the first distillation column was operated under conditions in which the temperature of the column top of the first distillation column was 53° C.; the temperature of a column bottom of the first distillation column was 73° C.; and the pressure of the column bottom was −3 kPaG. A fraction $F_1$ mainly containing methacrolein and methanol was extracted from a fifth stage position as counted from the column top of the distillation column. The fraction $F_1$ had a composition containing 14.4% by mass of methacrolein, 63.8% by mass of methanol, 5.8% by mass of methyl acrylate, and 11.6% by mass of methyl methacrylate. 96.9% by mass of the methacrolein and 78.8% by mass of the methanol supplied to the distillation column could be collected in the distillation column. The fraction as a reaction raw material was recycled to the methacrolein absorber column. A column bottom liquid was collected from the column bottom of the first distillation column. In the collected column bottom liquid, the concentration of the methanol was 14.8% by mass; the concentration of the methyl acrylate was 0.5% by mass; and the concentration of the water was 16.1% by mass. The concentration of the methanol in a condensate obtained by condensing a column top gas was 22.3% by mass. The residence time of the column bottom liquid in the first distillation column was 5 minutes.

The first distillation column was continuously operated on the above-mentioned conditions. As a result, increase in a differential pressure between trays of the first distillation column and increase in a differential pressure in a reboiler did not occur over one year, which allowed a continuous operation. No occurrence of the increase in the differential pressure between the trays and the increase in the differential pressure in the reboiler suggests that a polymer does not occur between the trays in the reboiler. It is assumed that the continuous operation was achieved by virtue of no occurrence of the polymer. When the distillation column and the reboiler were opened and visually checked after the operation for one year, remarkable adhesion of the polymer was not observed in the device.

In the above-mentioned operation, an operation after collecting the column bottom liquid was as follows. That is, when sulfuric acid was added to the column bottom liquid collected from the first distillation column to adjust the pH of the column bottom liquid to 3, and the column bottom liquid was supplied to a phase separator, the column bottom liquid could be immediately separated into a light phase containing the methyl methacrylate and the methacrylic acid and a heavy phase containing the methanol and the water. The separated heavy phase was supplied to a second distillation column, and distilled to collect the methanol. After the above-mentioned one-year operation, the precipitation of alkali salts was not observed in the second distillation column.

As described above, the concentration of the methyl acrylate in the column bottom liquid collected from the first distillation column by distillation was 0.5% by mass, and the concentration of a medium boiling point material in the column bottom liquid was evaluated to be 0.1% by mass or more. 10.7% by mass of the methyl acrylate contained in the reaction solution was extracted from the bottom column, whereby the concentration of the methyl acrylate in the oxidative esterification reactor was not observed.

Example 2

A first distillation column was operated under the same conditions as those of Example 1 except that the temperature of a column top of the first distillation column was set to 53° C. and the temperature of a column bottom of the first distillation column was set to 72° C., to produce methyl methacrylate. The concentration of methanol in a column bottom liquid collected by distillation was 20.5% by mass. As a result of the operation in this state, as with Example 1, increase in a differential pressure between trays of the first distillation column and increase in a differential pressure in a reboiler did not occur, which allowed a continuous operation for one year. When the distillation column and the reboiler were opened and visually checked after the operation for one year, remarkable adhesion of a polymer was not observed in a device.

In the above-mentioned operation, an operation after collecting the column bottom liquid was as follows. That is, when sulfuric acid was added to the column bottom liquid collected from the first distillation column to adjust the pH of the column bottom liquid to 3, and the column bottom liquid was supplied to a phase separator, the column bottom liquid could be immediately separated into a light phase and a heavy phase. The separated heavy phase was supplied to a second distillation column, and distilled to collect the methanol. After the above-mentioned one-year operation, the precipitation of alkali salts was not observed in the second distillation column. The concentration of methyl acrylate in the column bottom liquid collected from the first distillation column by distillation was 0.7% by mass, and the concentration of a medium boiling point material in the column bottom liquid was evaluated to be 0.1% by mass or more. 15.4% by mass of the methyl acrylate contained in the reaction solution was extracted from a bottom column, whereby the concentration of the methyl acrylate in an oxidative esterification reactor was not observed. The average reaction yield of the methyl methacrylate for the one-year operation in an oxidative esterification reaction was equivalent to that of Example 1.

Example 3

A first distillation column was operated under the same conditions as those of Example 1 except that the temperature of a column top of the first distillation column was set to 53° C. and the temperature of a column bottom of the first distillation column was set to 76° C., to produce methyl methacrylate. The concentration of methanol in a column bottom liquid collected by distillation was 7.6% by mass. As a result of the operation in this state, as with Example 1, increase in a differential pressure between trays of the distillation column and increase in a differential pressure in a reboiler did not occur for one year, which allowed a continuous operation. When the distillation column and the reboiler were opened and visually checked after the operation for one year, remarkable adhesion of a polymer was not observed in a device.

In the above-mentioned operation, an operation after collecting the column bottom liquid was as follows. That is, when sulfuric acid was added to the column bottom liquid collected from the first distillation column to adjust the pH of the column bottom liquid to 3, and the column bottom liquid was supplied to a phase separator, the column bottom liquid could be immediately separated into a light phase and a heavy phase. The separated heavy phase was supplied to a second distillation column, and distilled to collect the methanol. After the above-mentioned one-year operation, the precipitation of alkali salts was not observed in the second distillation column. The concentration of methyl acrylate in the column bottom liquid collected from the first distillation column by distillation was 0.3% by mass, and the concentration of a medium boiling point material in the column bottom liquid was evaluated to be 0.1% by mass or more. Only 4.8% by mass of the methyl acrylate contained in the reaction solution was extracted from the bottom column, whereby the methyl acrylate was concentrated in an oxidative esterification reactor. As a result, the average reaction yield of the methyl methacrylate for the one-year operation was reduced by 1.4% by mass compared with Example 1, but there was no problem for the practical use.

Example 4

A first distillation column was operated under the same conditions as those of Example 1 except that the temperature of a column top of the first distillation column was set to 53° C. and the temperature of a column bottom of the first distillation column was set to 71° C., to produce methyl methacrylate. The concentration of methanol in a column bottom liquid collected by distillation was 27.5% by mass. As a result of the operation in this state, increase in a differential pressure between trays of the distillation column and increase in a differential pressure in a reboiler did not occur for one year, which allowed a continuous operation. When the distillation column and the reboiler were opened and visually checked after the operation for one year, remarkable adhesion of a polymer was not observed in a device.

In the above-mentioned operation, an operation after collecting the column bottom liquid was as follows. That is, sulfuric acid was added to the column bottom liquid collected from the first distillation column to adjust the pH of the column bottom liquid to 3, and the column bottom liquid was supplied to a phase separator. As a result, the column bottom liquid could be separated into a light phase and a heavy phase, but a time required for separation was remarkably increased. Furthermore, when the separated heavy phase was observed, alkali salts were confirmed to be slightly precipitated. When water was added to the heavy phase, the heavy phase was easily dissolved. After the above-mentioned one-year operation, the precipitation of alkali salts was slightly observed in a second distillation column, but there was no problem for the practical use. Furthermore, the concentration of methyl acrylate in the column bottom liquid collected from the first distillation column by distillation was 1.0% by mass, and the concentration of a medium boiling point material in the column bottom liquid was evaluated to be 0.1% by mass or more. 24.6% by mass of the methyl acrylate contained in the reaction solution was extracted from the bottom column, whereby the concentration of the methyl acrylate in an oxidative esterification reactor was not observed. The average reaction yield of the methyl methacrylate for the one-year operation in an oxidative esterification reaction was equivalent to that of Example 1.

Example 5

A first distillation column was operated under the same conditions as those of Example 1 except that the temperature of a column top of the first distillation column was set to 53° C. and the temperature of a column bottom of the first distillation column was set to 79° C., to produce methyl methacrylate. The concentration of methanol in a column bottom liquid collected by distillation was 1.8% by mass. As a result of the operation in this state, increase in a differential pressure between trays of the distillation column and increase in a differential pressure in a reboiler did not occur for one year, which allowed a continuous operation. However, when the distillation column and the reboiler were opened and visually checked after the operation for one year, adhesion of a polymer was confirmed on the rear of a downcomer of a sieve tray.

In the above-mentioned operation, an operation after collecting the column bottom liquid was as follows. That is, when sulfuric acid was added to the column bottom liquid collected from the first distillation column to adjust the pH of the column bottom liquid to 3, and the column bottom liquid was supplied to a phase separator, the column bottom liquid could be immediately separated into a light phase and a heavy phase. The separated heavy phase was supplied to a second distillation column, and distilled to collect the methanol. After the above-mentioned one-year operation, the precipitation of alkali salts was not observed in the second distillation column. The concentration of methyl acrylate in the column bottom liquid collected from the first distillation column by distillation was 0.2% by mass, and the concentration of a medium boiling point material in the column bottom liquid was evaluated to be 0.1% by mass or more. Only 2.8% by mass of the methyl acrylate contained in the supply solution was extracted from the bottom column, whereby the methyl acrylate was concentrated in an oxidative esterification reactor. As a result, the average reaction yield of the methyl methacrylate for the one-year operation was reduced by 3.6% by mass compared with Example 1, but there was no problem for the practical use.

Comparative Example 1

A first distillation column was operated under the same conditions as those of Example 1 except that the temperature of a column top of the first distillation column was set to 53° C. and the temperature of a column bottom of the first distillation column was set to 84° C., to produce methyl methacrylate. The concentration of methanol in a column bottom liquid collected by distillation was 1570 mass ppm. When the operation was performed for three months in this state, a differential pressure of the distillation column and a differential pressure in a reboiler tube were increased, which tended to cause trays of the distillation column and a reboiler to be blocked, so that the operation was impossible. Therefore, the operation was stopped. As a result of check after the operation stop, the rear surface of the tray and the tube of the reboiler were blocked with a polymer derived from the methyl methacrylate. When sulfuric acid was added to the column bottom liquid collected from the first distillation column to adjust the pH of the column bottom liquid to 3, and the column bottom liquid was supplied to a phase separator, the column bottom liquid could be immediately separated into a light phase and a heavy phase. The concentration of methyl acrylate in the column bottom liquid was 80 mass ppm, and the concentration of a medium boiling point material in the column bottom liquid was evaluated to be about 232 mass ppm (less than 0.1% by mass). Only 0.1% by mass of the methyl acrylate contained in the reaction solution was extracted from the bottom column, whereby the methyl acrylate was concentrated in an oxidative esterification reactor. The reaction yield of the methyl methacrylate was gradually reduced, and the average reaction yield of the methyl methacrylate for the one-year operation was reduced by 5.6% by mass compared with Example 1.

Comparative Example 2

A first distillation column was operated under the same conditions as those of Example 1 except that the temperature of a column top of the first distillation column was set to 53° C. and the temperature of a column bottom of the first distillation column was set to 70° C., to produce methyl methacrylate. The concentration of methanol in a column bottom liquid collected by distillation was 32.0% by mass.

In the above-mentioned operation, an operation after collecting the column bottom liquid was as follows. That is, when sulfuric acid was added to the column bottom liquid collected from the first distillation column to adjust the pH of the column bottom liquid to 3, and the column bottom liquid was supplied to a phase separator, the column bottom liquid formed a homogeneous phase, so that the column bottom liquid could not be separated into a light phase and a heavy phase in the next step of the distillation column. Furthermore, when the column bottom liquid was observed, alkali salts were confirmed to be precipitated in large amounts, and even if water was added in the same manner as in Example 4, all the alkali salts were not dissolved. As a result, the alkali salts were precipitated in large amounts in a second distillation column, which caused pipings and trays to be blocked, so that the operation was impossible. Thus, the operation of the second distillation column was impossible, so that the concentration of methyl acrylate and the reaction yield of the methyl methacrylate in an oxidative esterification reactor could not be evaluated.

REFERENCE SIGNS LIST

1: methacrolein absorber column
2: oxidative esterification reactor
3: first distillation column
4: phase separator
5: second distillation column
6: first heat exchanger unit
7: second heat exchanger unit
10: producing device

The invention claimed is:

1. A method for producing methyl methacrylate, comprising:
   a distillation step comprising
      supplying a reaction solution, which is obtained by subjecting methacrolein, methanol, and molecular oxygen to oxidative esterification in an oxidative esterification reactor and which comprises the methyl methacrylate as a reaction product, to a first distillation column located at downstream of the oxidative esterification reactor,
      extracting a fraction comprising the methacrolein and the methanol from a medium section of the first distillation column, and
      extracting a column bottom liquid comprising the methyl methacrylate from a column bottom of the first distillation column,
   wherein a concentration of the methanol in the column bottom liquid is 1% by mass or more and 30% by mass or less.

2. The method for producing methyl methacrylate according to claim 1, further comprising a step of phase-separating the column bottom liquid into a light phase and a heavy phase.

3. The method for producing methyl methacrylate according to claim 2, further comprising a step of distilling the heavy phase in a second distillation column to obtain a fraction comprising the methanol.

4. The method for producing methyl methacrylate according to claim 3, wherein the fraction comprising the methanol obtained from the second distillation column is recycled to the oxidative esterification reaction.

5. The method for producing methyl methacrylate according to claim 2, further comprising
   a step of subjecting the light phase to purification, and
   a step of adding a polymerization inhibitor to the light phase after the purification.

6. The method for producing methyl methacrylate according to claim 1, further comprising a step of subjecting the methacrolein, the methanol, and the molecular oxygen to oxidative esterification in the oxidative esterification reactor, to obtain the reaction solution.

7. The method for producing methyl methacrylate according to claim 1, wherein the fraction, which comprises the methacrolein and the methanol and which has been extracted from the medium section of the first distillation column, is recycled to the oxidative esterification reaction.

8. The method for producing methyl methacrylate according to claim 1, wherein a methanol is further added to the first distillation column in the distillation step to adjust the concentration of the methanol in the column bottom liquid.

9. The method for producing methyl methacrylate according to claim 8, wherein a ratio of the number of moles of the methanol to be further added, to the number of moles of the methacrolein contained in the reaction solution is 0.1 or more and 3.0 or less.

10. The method for producing methyl methacrylate according to claim 1, wherein, in the distillation step, a temperature of the column bottom of the first distillation column is 45° C. or higher and 80° C. or lower, and a pressure of the column bottom of the first distillation column is −50 kPaG or more and 0 kPaG or less.

11. The method for producing methyl methacrylate according to claim 1, wherein a residence time of the column bottom liquid of the first distillation column calculated by the following formula is 1.5 hours or less:
   residence time (hour)=amount (kg) of column bottom liquid present in first distillation column/extraction amount (kg/hour) of column bottom liquid per unit time.

12. The method for producing methyl methacrylate according to claim 1, wherein a concentration of an intermediate boiling point material in the column bottom liquid in the first distillation column is 0.1% by mass or more.

13. The method for producing methyl methacrylate according to claim 12, wherein the intermediate boiling point material comprises methyl acrylate.

14. The method for producing methyl methacrylate according to claim 1, wherein at least a part of the column bottom liquid is extracted, then heated by a heat-exchange with a vent gas generated from the oxidative esterification reactor, and thereafter returned to the column bottom of the first distillation column.

15. The method for producing methyl methacrylate according to claim 1,
   wherein:
   an amount of the methacrolein extracted from the medium section of the first distillation column is 95% by mass or more of an amount of the methacrolein contained in the reaction solution; and
   an amount of the methanol extracted from the medium section of the first distillation column is 70% by mass or more of an amount of the methanol contained in the reaction solution.

16. The method for producing methyl methacrylate according to claim 1, further comprising a step of cooling a column top gas out of the first distillation column to obtain a condensate,
   wherein a concentration of the methanol in the condensate is 30% by mass or less.

* * * * *